(12) United States Patent
DiLorenzo et al.

(10) Patent No.: US 12,139,239 B2
(45) Date of Patent: *Nov. 12, 2024

(54) ANTI-FOULING SYSTEM FOR SUBMERGED STRUCTURES AND METHOD FOR PREVENTING BIOFOULING

(71) Applicant: WAVEARRAY ANTIFOULING SYSTEMS, LLC, Naples, FL (US)

(72) Inventors: James DiLorenzo, Naples, FL (US); Sydney Innes, Fort Meyers, FL (US); Justin Mullins, Naples, FL (US); Jake Levere, Naples, FL (US); Peter Schibly, Litchfield, NH (US); Geoff Trager, Naples, FL (US)

( * ) Notice: Subject to any disclaimer, the term of this patent is extended or adjusted under 35 U.S.C. 154(b) by 158 days.

This patent is subject to a terminal disclaimer.

(21) Appl. No.: 17/525,889

(22) Filed: Nov. 13, 2021

(65) Prior Publication Data

US 2022/0153395 A1 May 19, 2022

Related U.S. Application Data

(60) Provisional application No. 63/113,925, filed on Nov. 15, 2020.

(51) Int. Cl.
*B63B 59/04* (2006.01)
*G01N 33/18* (2006.01)

(52) U.S. Cl.
CPC .......... *B63B 59/04* (2013.01); *G01N 33/1886* (2013.01)

(58) Field of Classification Search
CPC .......... H04R 1/20; B63B 59/04; A01M 29/22; A01M 29/16
See application file for complete search history.

(56) References Cited

U.S. PATENT DOCUMENTS

| | | | | |
|---|---|---|---|---|
| 4,943,954 A | * | 7/1990 | Ostlie | B63B 59/04 181/0.5 |
| 5,143,011 A | * | 9/1992 | Rabbette | B63B 59/04 114/222 |
| 5,735,226 A | * | 4/1998 | McNeal | B63B 59/04 134/1 |
| 7,211,173 B1 | * | 5/2007 | Staerzl | B63B 59/04 204/196.18 |

(Continued)

FOREIGN PATENT DOCUMENTS

| | | | | | |
|---|---|---|---|---|---|
| CA | 2948991 A1 | * | 5/2018 | | |
| GB | 2496397 A | * | 5/2013 | ............. | B63B 59/04 |
| WO | WO-2012085630 A1 | * | 6/2012 | ............. | B08B 17/02 |

*Primary Examiner* — Luke D Ratcliffe
(74) *Attorney, Agent, or Firm* — Andrew Morabito

(57) ABSTRACT

A method of preventing fouling of a submerged structure, the method comprising: activating, by one or more computing devices, at least one transducer and at least one sensor attached to a structure; monitoring, by one or more computing devices, data collected by the at least one sensor related to the submerged structure and the salinity of the water; generating, by one or more computing devices, a predetermined sound wave from the at least one transducer based on the data collected by the at least one sensor; altering, by one or more computing devices, the at least one transducer based collected data from the at least one sensor; and autonomously adjusting, by one or more computing devices, at least one of the at least one transducer.

15 Claims, 5 Drawing Sheets

(56) References Cited

U.S. PATENT DOCUMENTS

| | | | | |
|---|---|---|---|---|
| 11,242,121 B2 * | 2/2022 | DiLorenzo | ............. | B08B 7/026 |
| 2009/0314193 A1 * | 12/2009 | Groves | ................ | B63B 59/04 |
| | | | | 114/222 |
| 2019/0135389 A1 * | 5/2019 | DiLorenzo | ............. | B08B 7/026 |

* cited by examiner

ANTI-FOULING SYSTEM FOR SUBMERGED STRUCTURES AND METHOD FOR PREVENTING BIOFOULING

CROSS-REFERENCE TO RELATED APPLICATIONS

This application is a continuation-in-part (and claims the benefit of priority under 35 USC 120) of U.S. application No. 63/113,925, filed Nov. 15, 2020. The disclosure of the prior applications is considered part of (and is incorporated by reference in) the disclosure of this application.

BACKGROUND OF THE INVENTION

The present invention relates to a method for preventing aquatic biological growth on submerged structures and/or biological fouling in water (e.g., fouling organisms found in ship ballast tanks), and more particularly to a system designed to be self-monitoring and controlling related to submerged structures.

The settlement and growth of fouling organisms such as barnacles and algae have long plagued both commercial and recreational boaters. The colonization of submerged man-made surfaces by these organisms is referred to as "fouling" as the organisms are dangerous and destructive to the structure. In addition, fouling is prevalent and widespread on marina pilings, and other structures. On fixed structures, fouling increases weight and structural loading.

Various methods have been used to attempt to limit boat fouling, such as anti-fouling paints, the use of copper electrodes to release copper into the water and use of chlorine generation to release chlorine into the water. In general, these techniques function by releasing toxic chemicals into the water surrounding a boat thus preventing the settlement and subsequent growth of barnacles as well as other forms of marine, brackish and freshwater life. However, the use of these methods obviously creates a negative environmental impact affecting fish-life and in turn fish food and humans and poses a serious threat to the health of the world oceans and other bodies of water due to the toxicity of chemicals employed. Several states in the U.S. have now banned the use of certain anti-fouling agents and other countries of the world have joined in a similar ban.

Each of these anti-fouling methods as now practiced have problems discovered by the present inventors and resolved by their invention. As a result, many boaters have resorted to installing expensive lifts to remove their boats from the water in areas such as Florida, where year-round boating is common. For larger boats (e.g., over 35 feet), lifts are often not practical or affordable. And in many places worldwide, lifts are not commonly used due to seasonal boating activities.

In consideration of the current existing anti-fouling methods and practices, which include primarily the application of toxic bottom paints to boats and labor intensive, repetitive manual cleaning of fouled surfaces, both of which are only partially effective and provide short-term protection only, it is evident there remains the need for a system that incorporates the attributes of affordability, long-term consistent fool proof operability, dependability and effectiveness, as well as being safe for the environment.

SUMMARY

In a first embodiment, the present invention is an a method of preventing fouling of a submerged structure, the method comprising: activating, by one or more computing devices, at least one transducer and at least one sensor attached to a structure; monitoring, by one or more computing devices, data collected by the at least one sensor related to the submerged structure and the salinity of the water; generating, by one or more computing devices, a predetermined sound wave from the at least one transducer based on the data collected by the at least one sensor; altering, by one or more computing devices, the at least one transducer based collected data from the at least one sensor; and autonomously adjusting, by one or more computing devices, at least one of the at least one transducer.

In a second embodiment, the present invention is an a computer program product for autonomously preventing fouling of a submerged structure, the computer program product comprising a computer readable storage medium having program instructions embodied therewith, the program instructions executable by a computing device to cause the computing device to: program instructions to activate a at least one transducer and at least one sensor attached to a structure; program instructions to monitor data collected by the at least one sensor related to the submerged structure; program instructions to generate a predetermined sound wave from the at least one transducer based on the data collected by the at least one sensor; program instructions to alter the at least one transducer based collected data from the at least one sensor; and program instructions to adjust at least one of the at least one transducer.

In a third embodiment, the present invention is an a system for autonomously preventing fouling of a submerged structure comprising: a CPU, a computer readable memory and a computer readable storage medium associated with a computing device; program instructions to activate a at least one transducer and at least one sensor attached to a structure; program instructions to monitor data collected by the at least one sensor related to the submerged structure; program instructions to generate a predetermined sound wave from the at least one transducer based on the data collected by the at least one sensor; program instructions to alter the at least one transducer based collected data from the at least one sensor; and program instructions to adjust at least one of the at least one transducer.

DETAILED DESCRIPTION OF THE INVENTION

Figure 1A:
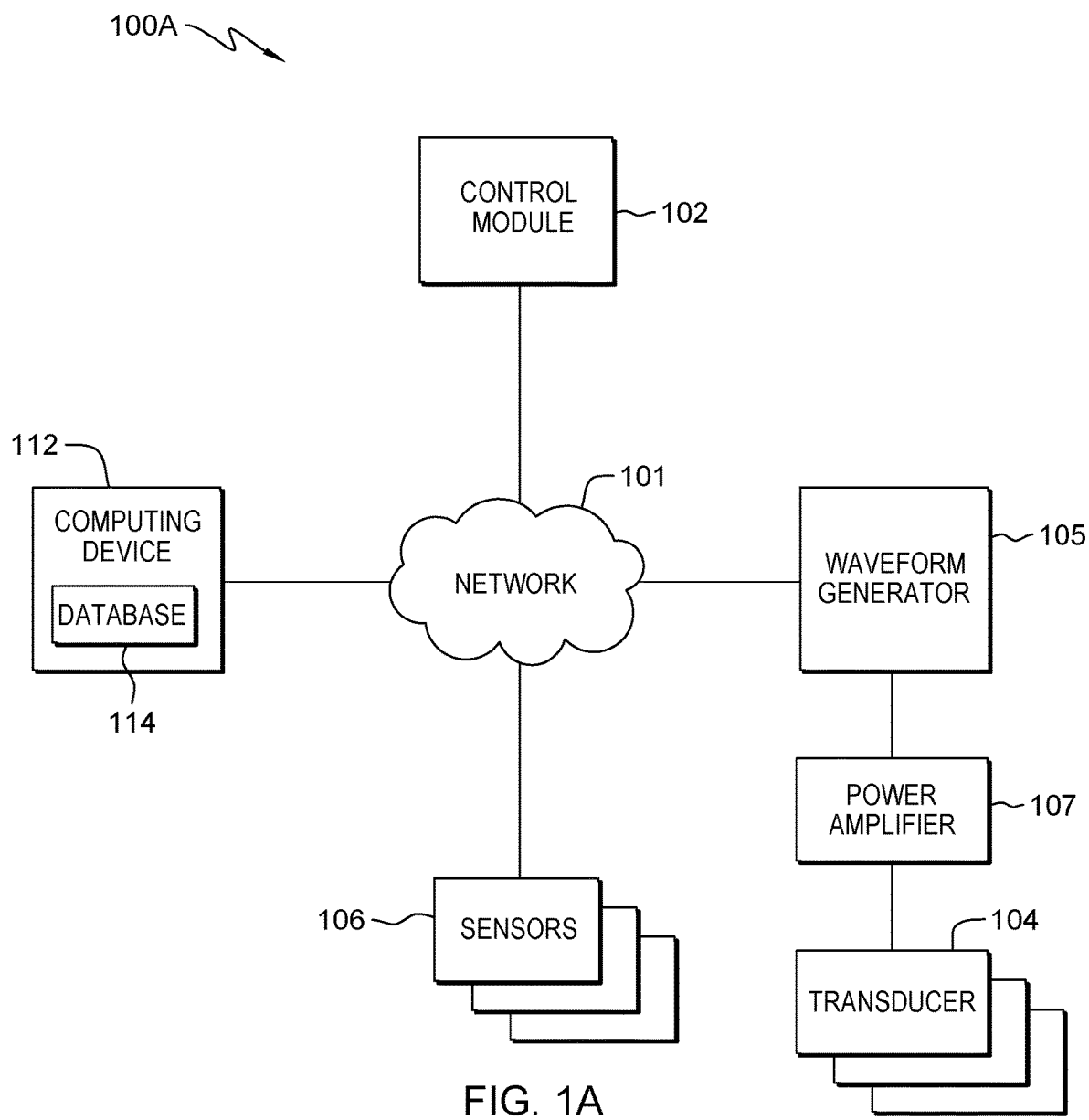
FIG. 1A depicts block diagram of a computing environment, in accordance with one embodiment of the present invention.

The present invention provides a non-toxic, environmentally beneficial anti-fouling system that is self-monitoring and self-adjusting. The present invention may prevent the fouling organism from growing, reducing the growth rate of the fouling organisms, may remove the fouling organisms from the structure, or a combination of these. Aspects of the present invention improve the effectiveness and reliability of systems employing sound energy to reduce or prevent marine, brackish and freshwater fouling on submerged structures. This invention makes use of a systems approach to generate, monitor, and control sound pressure near and around the hull of the submerged structures which are colonized by fouling organisms, by creating a vibrational energy field. This allows the submerged surface of a structure to remain free of fouling organisms in any aquatic environment.

The entire diverse and complex community of fouling organisms that settle and grow on ship surfaces, ranging from the tiniest micro-organisms (bacteria and algae) to the larger invertebrate larvae (barnacles, mussels, tunicates, bryozoans . . . etc.) can be targeted by delivering protective sound energy over the broad band of frequencies required to ensure maximum effectiveness on organisms differing widely in size. The sonic irradiations can be maintained continuously within optimum functional ranges for the entire suite of fouling community organisms with a concurrently operating monitoring, feedback, and adjustment system.

The present invention also provides the advantage of protecting submerged structures (e.g., pier pilings) from ship worms, barnacles, mussels, algae, and other fouling organisms. Through a modular and easily reconfigured system, the present invention provides an advantage of being highly customizable based on the intended application. The present approach entails the utilization of various sensors for autonomously controlling an array of transducers or array of arrays of transducers. This provides for a system that maximizes the performances of the arrays of transducers to the greatest degree possible. Also, the inventive system can be used to keep water intake pipes of power plants and other operations free of serious pest organisms like zebra mussels (*Dreissena polymorpha*) which settle inside and outside the pipe the pipe, grow rapidly, and clog such pipes. This prevents the environmentally damaging introduction and spread of exotic, invasive fouling organisms to new waters when ballast water is released. Invasive species are now considered a major threat to the health of world ocean ecosystem stability and biodiversity.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

The present invention is disclosed in a first embodiment depicted in FIG. 1A, in accordance with one embodiment of the present invention. The system 100, is comprised of a network 101, a control module 102, at least one transducer 104, at least one sensor 106, a waveform generator 105, a power amplifier 107, and a computing device 112. In the depicted system 100 each component may have its own independent power source, the system may have a single power source, or a mixture of both may be employed.

Figure 1B:
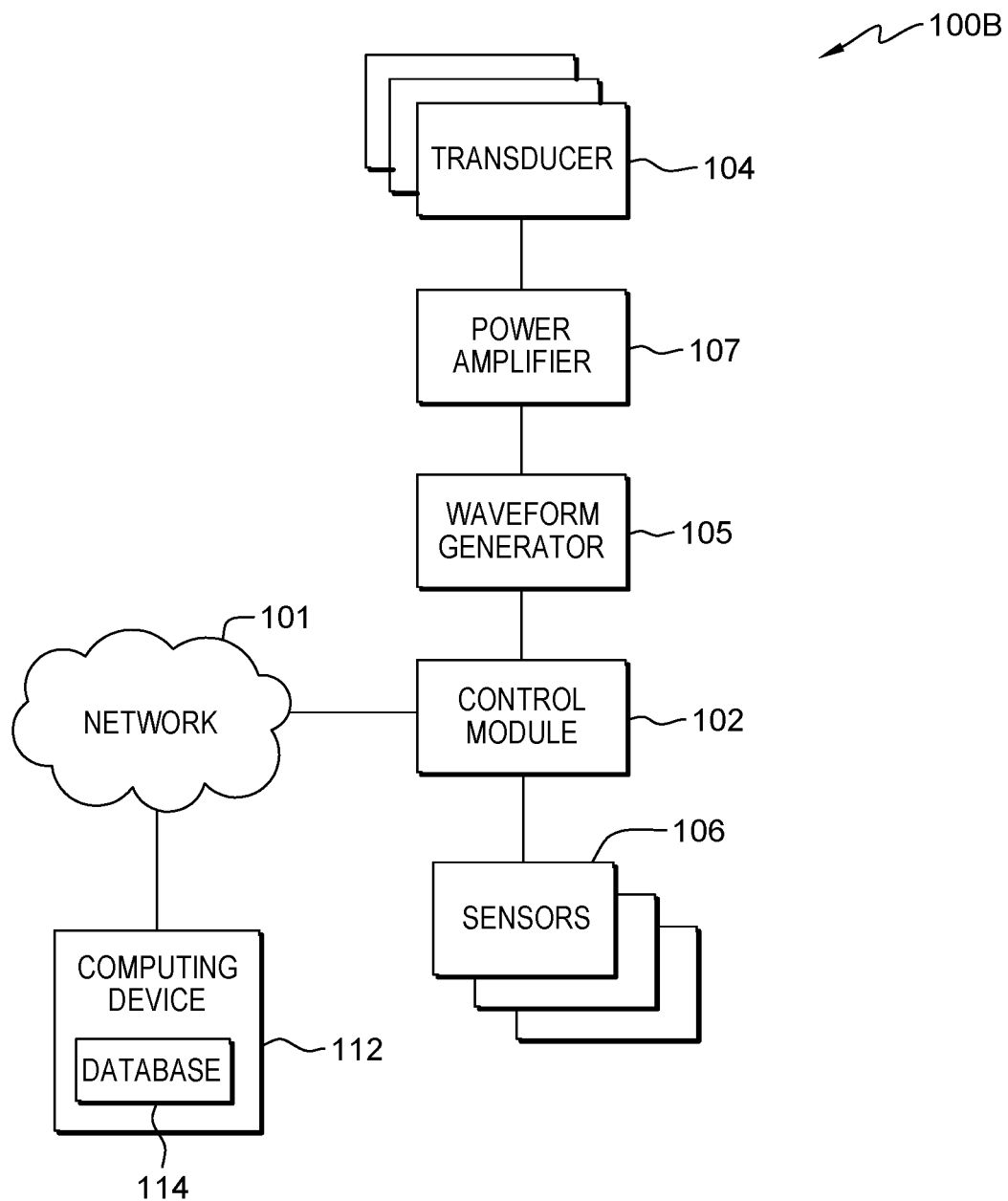
FIG. 1B depicts block diagram of a computing environment, in accordance with one embodiment of the present invention.

The present invention is depicted in a second embodiment in FIG. 1B, wherein the control module 102, is connected in a private circuit with the waveform generator 105, the power amplifier 107, the transducer 104, and the sensor 106. The control module 102 is able to communicate with the computing device 112 via network 101. This is another embodiment, of the design of system 100.

Network 101 may be a local area network (LAN), a wide area network (WAN) such as the Internet, any combination thereof, or any combination of connections and protocols that can support communications between the computing device and the control module 102. Network 101 may include wired, wireless, fiber optic, or other forms of data exchanging connections. In other embodiments, the network 101 may represent a server computing system utilizing multiple computers as a server system, such as in a cloud computing environment. In another embodiment. In the depicted embodiment, the control module 102, the waveform generator 105, the power amplifier 107, the sensors 106, and the transducers 104 are all connected through a wired network. In additional embodiments, the control module 102, the waveform generator 105, the power amplifier 107, the sensors 106, and the transducers 104 may be connected by a local area network, such as but not limited to, Bluetooth® technology or other wireless networks.

The control module 102 controls and monitors the transducers 104 and analyzes the data collected by the sensors 106. The control module 102 monitors all aspects of the system and determines the mode of the system, e.g., active or standby based on the submerged structure and the area of coverage, if there is any bio-fouling present on the submerged structure, or user request. The control module 102 processes the data collected by the sensors 106 to determine the optimum settings for the transducers 104. The control module 102 is able to adjust the transducers 104 or the mount which the transducers 104 are attached to, based on the received data.

The control module 102 may be a standalone computing device or may be part of a computing system that provides the commands for the transducers 104 and processes the data collected by the sensors 106. The control module 102 may be a management server, a web server, or any other electronic device or computing system capable of processing program instructions and receiving and sending data. In other embodiments, the control module 102 may be a laptop computer, tablet computer, netbook computer, personal computer (PC), a desktop computer, or any programmable electronic device capable of communicating with the transducers 104 and the sensors 106 either directly (i.e., wired) or remotely (i.e., wirelessly). In other embodiments, control module 102 may be a server computing system utilizing multiple computers as a server system, such as in a cloud computing environment.

The transducers 104 are devices that are able to convert electrical waveforms into acoustic waves. The transducers 104, which can be constructed of piezoelectric transducers, of either ceramic crystalline type, or film organic material type. Each transducer 104 has the ability to vary the amplitude, frequency, volume, wave form, and sound-delivery pattern response, from approximately 20 kHz to about 50 kHz. Depending on the organisms (type, size, and settlement location), different sound waves may provide a more efficient and effective anti-fouling ability of the transducers 104. Through electrical impulses received from a wave form generator 105, the fluctuating voltage applied across the transducer 104 causes a crystal to expand and contract, which in turn causes oscillation at a frequency determined by the waveform generator 105. The crystal used in the transducer 104 may be but not limited to, berlinite, quartz, tourmaline, salt, and the like which would be acceptable to use in a submerged environment. This voltage fluctuation in turn produces a mechanical (e.g., up-and-down) vibration of a surface of the transducer 104, causing sound waves to propagate through the environment.

The mechanical sound waves travelling from the transducer 104 consist of moving bands of compressed fluid (high pressure) alternating with bands of rarified or expanded fluid (low pressure). If the pressure differential between the compressed and rarified zones is great enough and occurs rapidly enough (i.e., if the sound is "loud" enough and the frequency is high enough), cavitation occurs. Cavitation is the formation of micro-bubbles from dissolved gases in a travelling rarified fluid band of the sound wave, followed by rapid compression of the bubbles to the point of implosion by the compressed fluid band that comes after the rarified one. The imploding bubbles cause shock waves and violent molecular motion of air or water on a micro-scale. If cavitation occurs right at the surface of a solid submerged object (e.g., boat hull or submerged structure) the high energy shock waves and extreme micro-turbulence make it substantially impossible for fouling organisms (e.g., tiny barnacle larvae, microscopic algae spores) to attach. These oscillations may be subsonic, audible, ultrasonic, or mega sonic frequencies. The transducers 104 are able to be electronically adjusted similar to that of a phased array. Each of the transducers 104 are able to produce a soundwave (e.g., beam). A single transducer 104 is able to produce a beam in one direction. However, if a plurality of transducers 104 are positioned next to one another (e.g., an array), the direction of the beam is adjustable. In situations where there is more than one transducer 104, the control module 102 is able adjust the settings of the transducer 104, and thus adjust the direction of the beam. With the ability to adjust the settings of the transducers 104, the beam is able to be directed at a plurality of positions within a zone of coverage. Wherein the direction of the sound waves generated by the transducers 104 are shifted the phase of each transducer 104 to redirect the sound wave. In some embodiments, the transducers 104 have the ability to shift the sound wave 90 degrees from center. Wherein center is perpendicular to the forward face of the transducer 104. In embodiments, where the transducers 104 are able to be electronically controlled, a phase shifter is integrated into the transducers 104 or may be incorporated as an independent component in the system 100.

The transducers 104 may be, but not limited to a piezoelectric ceramic transducer, or other types of transducers which are able to operate in a submerged environment. In some embodiments, the range of frequencies of the transducers 104 may be as low as 20 kHZ or as high as 1 MHz The transducers 104 are designed to operate with a low voltage supply. In one embodiment, that is a voltage has a pike of a hundred (100) voltage or a root mean square voltage of approximately thirty-five (35) volts. In additional embodiments, the low voltage supply may be higher or lower based on the intended operation and size of the system 100. This low voltage provides the benefit of reducing operating energy demand, the risk of injury to humans or wildlife in the water, and also reduce the likelihood of damage to the structure. The voltage of the transducers 104 is based on the electrical impedance of that transducer. The electrical impedance is determined by both the mechanical resistance presented to the transducer from its environment, e.g., materials on the transducer face, materials used to make a housing, whether it is operating in air or water or some other material such as the fiberglass of a boat hull, or epoxies or other adhesives use to make acoustic windows for a housing. In one embodiment, the transducers 104 are comprised of a transducer mounted (e.g., with epoxy) to a thin flexible diaphragm. The diaphragm with the transducer was then mounted in a housing that accommodates the exact size of the diaphragm on a "lip" and the diaphragm and transducer are sealed within the waterproof housing. In some embodiments, the diaphragm is one millimeter thick. In some embodiments, the transducers 104 produced an impedance of 200 Ohms to 500 Ohms with this low voltage.

The transducers 104 have a durable, water-proof housing, which has minimal impedance to the transmission of ultrasound through the fluid so that cavitation is induced at the target location. The direction and area of coverage of the transducer 104 is determined by the size, shape, contour, and overall design. Depending on the application various sizes of transducers 104 may be used.

Additionally, the design of the transducers 104 affects the distance at which the transducers 104 are operational. In one embodiment, the transducers 104 are designed to be effective at preventing fouling of the structure from one meter away.

In some embodiments, the transducers 104 are in an array formation, where multiple transducers 104 are used. The transducers 104 in the arrays may operate independently of one another or may operate as a single unit. In some embodiments the array formation is adjustable and has additional components such as a motor to control the array formation to traverse the structure remotely. The array of transducers 104 are electronically adjustable and controllable. This allows for the array to energize a large area via the mechanism of electronically sweeping the array focal point. In some embodiments, the transducers 104 are able to effectively prevent the fouling organisms from growing on the structure over an area of two square meters. Through the use of an array formation, and the ability to electronically adjust the array of transducers 104, a greater area is able to be covered without the necessity to move the transducers 104.

The power amplifier 107 is designed to increase the power input signal received by the transducer 104. The power amplifier 107 increase the amplitude of the signal received by the waveform generator 105. Various types of power amplifiers 107 known in the art may be employed in the system 100. In some embodiments, each transducer 104 has a power amplifier 107. In additional embodiments, one power amplifier 17 may be used for a plurality of transducers 104. The power amplifier 107 is configured to amplify an input signal from a waveform generator 105 which is capable of generating various waveforms. The power amplifier 107 needs to able to provide at least a variable voltage output of between 5 and 45 root-means-square (RMS) voltage, with a current capability of at least 1000 milliamps (ma) into an impedance of at least 120 ohms. The power amplifier 107 may be class AB, C, D, provided it is able to reproduce and amplify the waveforms input from the waveform generator 105. The power amplifier 107 has an impedance matching network which is capable of matching the impedance of the waveform generator 105. In one embodiment, the power amplifier 107 is a power FET type amplifier, which have the capability of high output power with good linearity. In some embodiments, the power amplifier 107 is designed with sufficient heat removal features and designs, as well as a waterproof enclosure. The power amplifier 107 may be a single channel, multiple channels, or the ability to bridge two channels. This allows for greater power capability into high impedance loads.

A waveform generator 105 is used to control the functionality of the transducers 104. The waveform generator 105 generates different types of electrical waveforms over a wide range of frequencies which are received by the transducer 104 and produce the acoustic wave to match the received electrical waveform. The waveform generator 105 uses numeric sequences to define the desired output waveform and is able to produce a multitude of different waveforms. In one embodiment, the waveform generator 105 is able produce a various different wave patterns (e.g., sine wave, square wave, sawtooth wave, etc.) from 20 kHz to 60 kHz.

The sensors 106 are devices which are able to receive data and transfer the data to the control module 102. In one embodiment, the sensors 106 convert acoustic energy (generated by the transducers 104) into electrical voltage. The converted acoustic energy is then analyzed with an analog to digital converted to provide a reading of the acoustic energy impinging on the sensor 106. In additional embodiments, the sensors 106 are able to detect temperature, humidity, barometric pressure, global positioning, wind, the systems power, and the like.

Computing device 112 may be a management server, a web server, or any other electronic device or computing system capable of processing program instructions and receiving and sending data. In other embodiments, the computing device 112 may be a laptop computer, tablet computer, netbook computer, personal computer (PC), a desktop computer, or any programmable electronic device capable of communicating with control module 102 via network 102. In one embodiment, computing device 112 represents a computing system utilizing clustered computers and components to act as a single pool of seamless resources.

Database 114 may be accessed by control module 102. Information gathered from the sensors 106, the waveform generator 105, the control module 102, and the transducers 104 may be stored to database 114. In one embodiment, database 114 is a database management system (DBMS) used to allow the definition, creation, querying, update, and administration of a database(s). In the depicted embodiment, database 114 resides on computing device 112. In other embodiments, database 114 resides on another server, or another computing device, provided that database 114 is accessible to control module 102.

Figure 2:
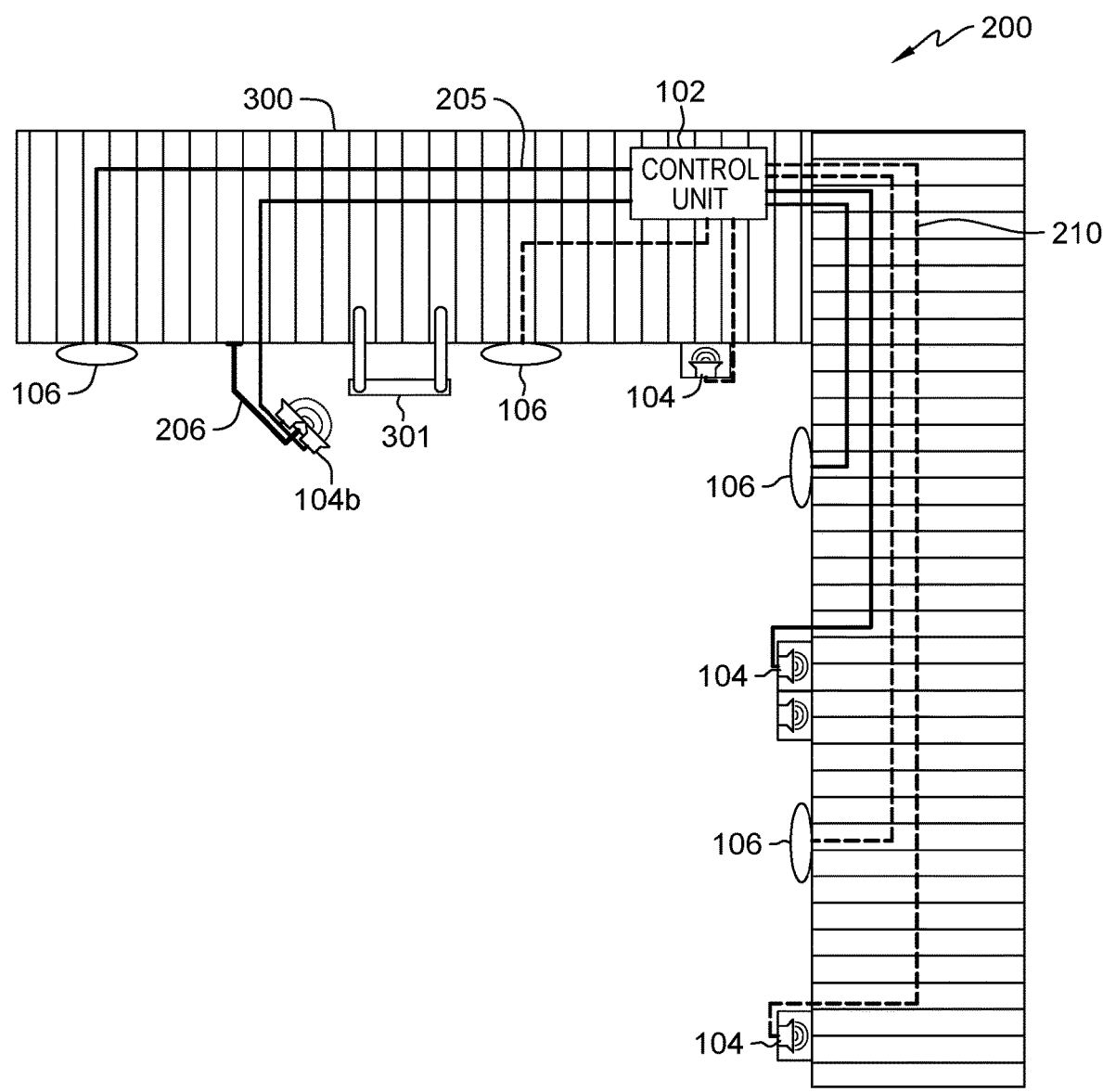
FIG. 2 depicts an image of an anti-fouling system for a submerged structure, in accordance with one embodiment of the present invention.
Figure 3:
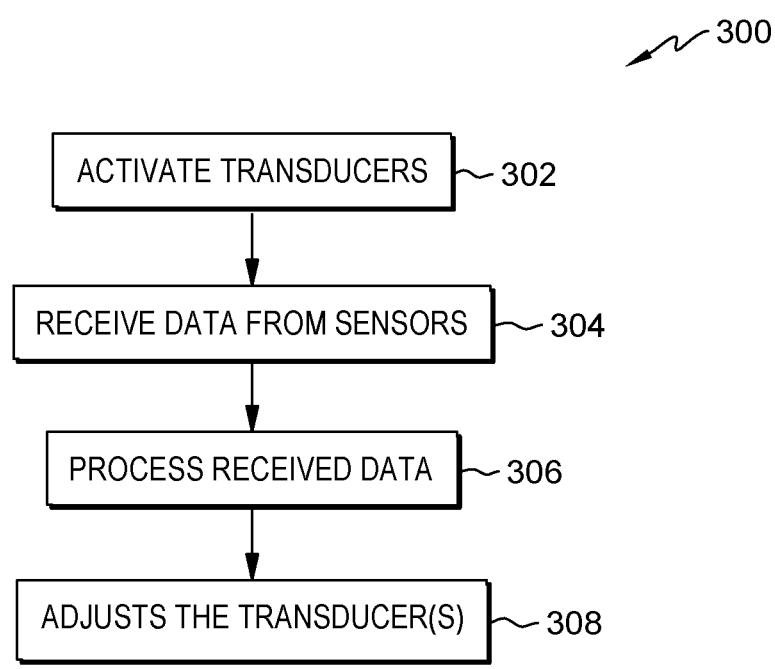
FIG. 3 depicts a flow diagram of the method of operation of the anti-fouling system, in accordance with one embodiment of the present invention.

The present invention is disclosed in an embodiment depicted in FIG. 2, in accordance with one embodiment of the present invention. In the depicted embodiment, the system is shown integrated into a dock 300. The system is comprised of a series of transducers 104, sensors 106, and a control unit 102. The sensors 106 and the transducers 104 are connected to the control unit via a wireless 201 connection or a wired connection 205. The sensors 106 and the transducers 104 may have internal or external power sources. The solid and dashed lines depicted wired (solid lines) connections and wireless (dashed lines) connections. The components of the system may be connected in a wired set up, a wireless setup, or a combination of both depending on the application. In the depicted embodiment, there is one control module 102 connected to a series of sensors 106 and a series of transducers 104. The sensors are positioned to detect the surface of the structure, and the transducers 104 are positioned to interact with the predetermined areas or regions of the surface(s) of the structure. In the depicted embodiment, one of the transducers 104 is an array and attached to the structure. There are additional transducers 104 attached to mounts which are connected to the structure to distance the transducers 104 away from the surface(s) of the structure. For example, transducer array 104B is attached to the dock 300 via a mount 206 and directed towards a ladder 301. The mount 206 may be stationary, or may be mechanically/electronically controlled so that the transducer array 104b can be moved when in use, and when not in use. The positioning of the transducers 104 is based on the intended coverage, type of transducers 104, and the like. The sensors 106 are positioned in a similar way to the transducers 104, directly mounted to the structure or attached to a mounting system. The mounting system allows for the transducers 104 and the sensors 106 to be positioned in the fluid and directed towards the structure. The mounting system allows for attachment to structure when in use, and removal for storage when not in use. The anti-fouling system is designed to be easily incorporated into any structure to provide the greatest coverage of the submerged structure to prevent the fouling organisms from growing. In one embodiment, the transducers 104 are positioned to allow for the irradiation of the surface of the structure which the operator intends to remain fouling organism free.

The sensors 106, are positioned in various locations based on the type of transducer 104 and the position of the transducer 104. In some embodiments, the sensors 106 are positioned next to the transducer 104, in front of the transducer 104, or other locations so that the sensor 106 can collect the sound energy data.

Sensory data is collected by the sensors 106 by the computing module 102. Sensory data collection is crucial for the control system to behave accordingly. Many different forms of measurements can be collected by the sensors 106 and stored in the database 114, including both external and internal measurements. External measurements can include but are not limited to reflected energy levels, temperature levels, mass salinity, sound-wave frequencies, sound pressure level and various measured distances. Internal measurements for the status of the array can include but is not limited to voltages applied, currents applied, temperature levels, frequencies and phase inputs. The autonomous array control is defined as the systems response to the sensory feedback with the objective of carrying out specific desired feedback mechanisms. Such a feedback mechanism can range from simple desired tasks to more sophisticated systems level tasks.

The transducers 104 and the sensors 106 can be configured in a plurality of different setups. In one embodiment, the mount may be stationary, and the array of transducers 104 are electronically adjustable. In another embodiments, the mount is mechanically adjustable and transducer(s) 104 are stationary and not electronically adjustable but are able to be physically repositioned due to the mounting system. In yet additional embodiments, the array of transducers 104 are electronically adjustable, and the mount is mechanically adjustable. This provides the advantage of reducing the number of transducers 104 required for the anti-foul of the structure. The fixture and extension can be attached to various parts of the structure and can be stowed when not in use. In additional embodiments, the transducer 104 and the sensors 106 are wirelessly connected to the computing module 104. Many other arrangements and configurations may be employed based on the intended operation, the structure to be protected from fouling, and requirements of the process. The system is designed to allow for the transducers 104 and the sensors 106 to communicate and activate autonomously only the transducers 104 which are necessary based on the size, position, and need of the structure. In some embodiments, the sensors 106 are in areas or region of the dock, and each of the sensors 106 in that region are related to a set of transducers 104 in that region. The system is designed to be independently controlled and require minimal human control. Based on the nature of the stationary (or slightly moving structure based on the movement of the water), the system can be set to run autonomously. They system can be designed to detect when a person is in the water near the transducers 104 to deactivate the transducers 104 when a person is exiting the water through a ladder or the like.

Figure 4:
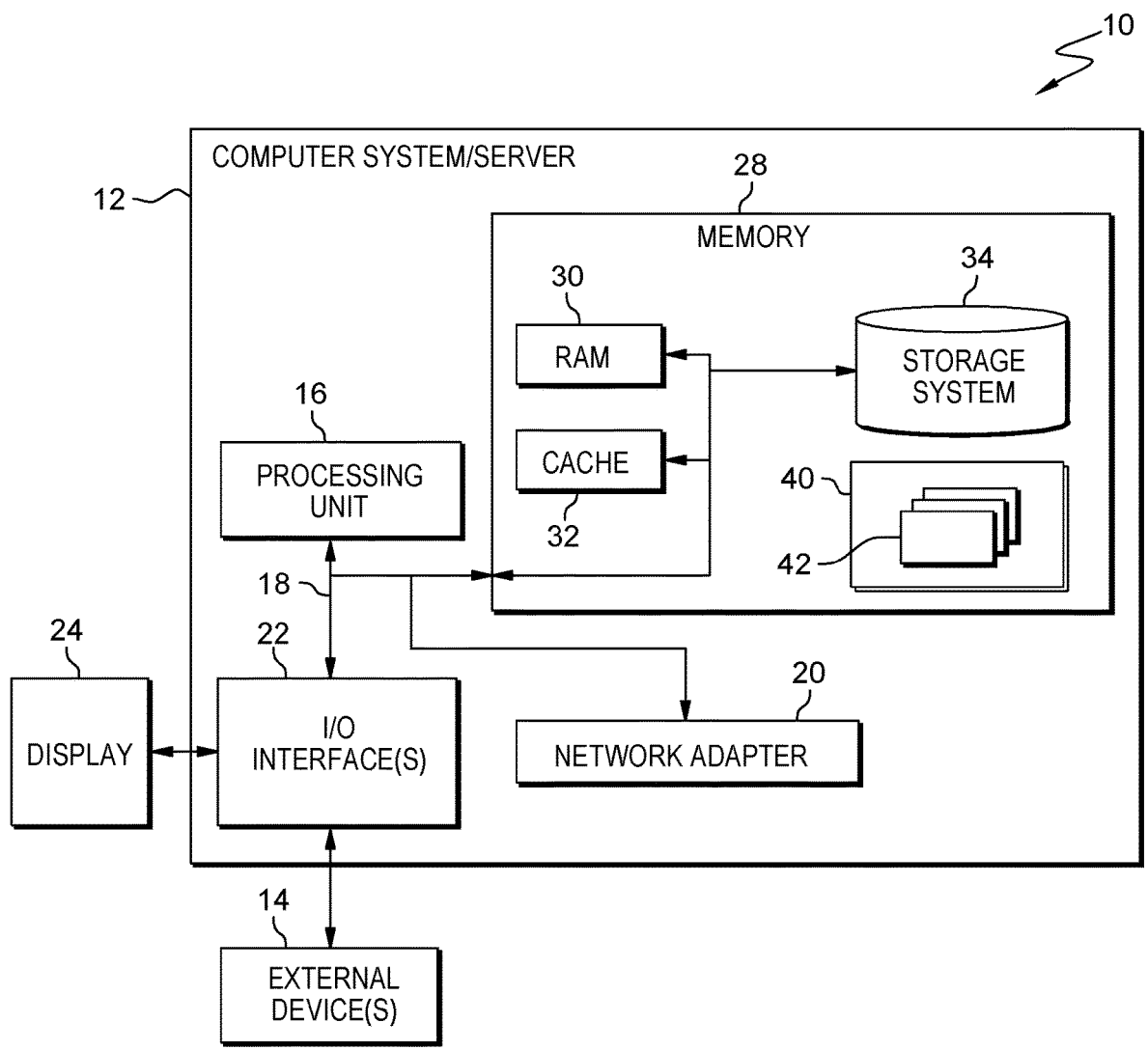
FIG. 4 depicts a block diagram depicting the internal and external components of the server and computing device of FIGS. 1A and 1B, in accordance with one embodiment of the present.

FIG. 4 depicts a flow diagram of the method of operation of the fouling system, in accordance with one embodiment of the present invention. The order or sequence of the process or method steps may be varied or re-sequenced according to alternative embodiments. Other substitutions, modifications, changes, and omissions may be made in the design, operating conditions and arrangement of the exemplary embodiments without departing from the scope of the present disclosure.

In step 302, the control module 102 activates a/the transducer(s) 104 once the system is activated either manually or automatically through the detection of the structure or a predetermined event occurring. The system may also test the water salinity and other characteristics of the water. The transducers 104 may be activated at a standard frequency based on the type of transducer 104 and the location of the transducer 104 after an initial reading if performed by the sensors 106. In step 304, the control module 102 receives data from the sensor 106 associated with each active transducer 104. In step 306, the control module 102 analyzes the received data. This allows the control module 102 to constantly know how each transducer 104 is performing based on the data collected by the sensors 106. In step 308, the control module 102 adjusts a/the transducer(s) 104 based on the received data to maintain a safe operation, a predetermined efficiency level, and a predetermined effective area so as to minimize the energy required by the system while maximizing the anti-fouling abilities of the system. Once the sensors 106 and the transducers 104 are setup near the structure, the sensor 106 detects the area of coverage of the transducers 104. The adjustment of the transducer 104 may be necessary to maintain an area of effectiveness for the prevention of fouling. This is vital as the constant changing of the fluid's conditions require constant adjustment of the transducers 104 to effectively protect the structure from fouling organisms.

As ultrasonic waves travel through water, they create cavitation bubbles that barnacle larvae and algae spores cannot travel through, preventing them from attaching to the protected surfaces. When the ultrasonic energy strikes a less massive object, it is believed that it may cause the object to "ring", and this ringing results in a fouling-free area over a majority of the object.

The control module 102 is able to adjust the direction of the beam produced by the transducers 104 by either adjusting the position of the transducers 104 on the mount, or if an array of transducers 104 are present, by electronically controlling the transducers 104 to adjust the direction of the beam. If the transducer 104 is attached to a movable mount, the control module 102 can adjust the physical positioning of the transducer 104 by repositioning the mount. This setup provides for a much greater adjustability of the area which the transducer 104 can cover versus a stationary setup of the transducer 104. If there is more than one transducer 104, the control module 102 can employ beam adjusting/steering technology to adjust the direction of the beam. By controlling the phase relationship of the excitation waveforms, the energy delivery (gain pattern) can be adjusted in specific directions. This beam adjusting/steering can focus energy on specific locations or be used to sweep the energy over a desired coverage area.

In additional embodiments, the control module 102 may detect stray electricity leaks into the fluid that may develop and consequently increase corrosion of boat metal parts (e.g., prop). If the electricity leak is detected the control module 102 may shut of the specific component or the entire system. Thus, an added feature of the monitoring part of system is corrosion protection.

By using a plurality of transducers 104 with a wide frequency response, the sweep and pulse patterns of sound delivery, the placement of the transducers 104, the use of sensors 106 to detect the sound energy and frequency being delivered to a given area of the structure, the use of control module 102 feedback analysis to measure and control the amplitude and frequency being delivered to various areas of the structures, the optimum frequency range and sound energy can be chosen to increase the effect, to the maximum prevention of fouling for a structure.

FIG. 4, computer system/server in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still, yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include but are not limited to: microcode, device drivers, redundant processing units, and external disk drive arrays, RAID systems, tape drives, and data archival storage systems, etc.

While this invention has been described in conjunction with the specific embodiments outlined above, it is evident that many alternatives, modifications and variations will be apparent to those skilled in the art. Accordingly, the preferred embodiments of the invention, as set forth above, are intended to be illustrative, not limiting. Various changes may be made without departing from the spirit and scope of this invention.

The present invention has been described in the foregoing on the basis of several preferred embodiments. Different aspects of different embodiments are deemed described in combination with each other, wherein all combinations which can be deemed by a skilled person in the field as falling within the scope of the invention on the basis of reading of this document are included. These preferred embodiments are not limitative for the scope of protection of this document. The rights sought are defined in the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

What is claimed is:

1. A method of preventing fouling of a submerged structure, the method comprising:
    activating, by one or more computing devices, at least one transducer and at least one sensor attached to a structure;
    monitoring, by one or more computing devices, data collected by the at least one sensor related to the submerged structure and the salinity of the water;
    generating, by one or more computing devices, a predetermined sound wave from each of the at least one transducers based on the data collected by the at least one sensor, wherein data collected includes an analysis of a surface contour of the submerged structures;
    adjusting, by one or more computing devices, the sound wave from the at least one transducer;
    altering, by one or more computing devices, a positioning or the sound wave produced by the at least one transducer based on collected data from the at least one sensor; and
    autonomously adjusting, by one or more computing devices, at least one of the at least one transducer.

2. The method of claim 1, further comprising, detecting, by one or more computing devices, the presence of an object between the at least one transducer and the submerged structure.

3. The method of claim 2, further comprising, deactivating, by one or more computing devices, the at least one transducer with an object detected.

4. The method of claim 1, further comprising, adjusting, by one or more computing devices, the direction of a beam produced by the at least one transducer based on a known target of the submerged structure.

5. A computer program product for autonomously preventing fouling of a submerged structure,
    the computer program product comprising a computer readable storage medium having program instructions embodied therewith, the program instructions executable by a computing device to cause the computing device to:
    program instructions to activate a at least one transducer and at least one sensor attached to a structure;
    program instructions to monitor data collected by the at least one sensor related to the submerged structure;
    program instructions to generate a predetermined sound wave from the at least one transducer based on the data collected by the at least one sensor;
    program instructions to alter the at least one transducer based collected data from the at least one sensor; and
    program instructions to adjust at least one of the at least one transducer,
    wherein if an object is detected between one of the at least one transducers and the submerged structure to deactivate that transducer.

6. The computer program product of claim 5, wherein the generating of the sound wave from the at least one transducer, further comprising, for a predetermined time based on a surface contour of the submerged surface.

7. The computer program product of claim 5, further comprising, program instructions to adjust the sound wave from the at least one transducer.

8. The computer program product of claim 5, further comprising, program instructions to adjust the at least one transducer, wherein the direction of a beam produced by the at least one transducer is redirected to a target location.

9. The computer program product of claim 5, further comprising, program instructions to collect data related to the salinity of the water.

10. A system for autonomously preventing fouling of a submerged structure comprising:
   a CPU, a computer readable memory and a computer readable storage medium associated with a computing device;
   program instructions to activate a at least one transducer and at least one sensor attached to a structure;
   program instructions to monitor data collected by the at least one sensor related to the submerged structure;
   program instructions to generate a predetermined sound wave from the at least one transducer based on the data collected by the at least one sensor;
   program instructions to alter the at least one transducer based collected data from the at least one sensor;
   program instructions to deactivate the at least one transducer with an object is detected between the submerged structure and the at least one transducer; and
   program instructions to adjust at least one of the at least one transducer.

11. The system of claim 10, wherein the generating of the sound wave from the at least one transducer, further comprising, for a predetermined time based on a shape of the submerged surface.

12. The system of claim 10, further comprising, program instructions to detect the presence of an object between the at least one transducer and the submerged structure.

13. The system of claim 10, further comprising, program instructions to adjust the sound wave from the at least one transducer.

14. The system of claim 10, further comprising, program instructions to adjust the direction of a beam produced by the at least one transducer based on a known location of the submerged structure.

15. The system of claim 10, further comprising, program instructions to adjust a mounting system based on the movement of the submerged structure detected by the at least one sensor.

* * * * *